United States Patent [19]
Comoglio et al.

[11] Patent Number: 6,030,949
[45] Date of Patent: Feb. 29, 2000

[54] MACROPHAGE STIMULATING PROTEIN FOR THE TREATMENT OF PATHOLOGIES OF THE NERVOUS SYSTEM

[75] Inventors: Paolo Comoglio; Alessandro Vercelli; Francesco Galimi; Gianfranco Caselli; Maria Cristina Stella, all of L'Aquila, Italy

[73] Assignee: Dompé S.p.A., L'Aquila, Italy

[21] Appl. No.: 09/084,233

[22] Filed: May 26, 1998

[30] Foreign Application Priority Data

May 28, 1997 [IT] Italy ................................ MI97A1247

[51] Int. Cl.⁷ .......................... A61K 38/00; A61K 38/16
[52] U.S. Cl. ............................ 514/12; 530/351; 435/68.1
[58] Field of Search .............................. 514/12; 530/351; 435/68.1

[56] References Cited

U.S. PATENT DOCUMENTS 5,696,086  12/1997  Avraham et al. ......................... 514/12

OTHER PUBLICATIONS

Santoro M M et al. Molecular And Cellular Biology, 16, No. 12, pp.7072–7083, Dec. 1996.

Ebens A et al. Neuron, 17, No. 6, p. 115, Dec. 1996.

Matsumoto K et al. J. of Biochemistry, 119, No. 4, pp. 591–600, Apr. 1996.

Nakamura T et al. Biochemical and Biophysical Research Communications, 224/2, p. 564–573, Feb. 1996.

Altaba et al. Mechanisms of Development, 60, No. 2, pp. 207–220, Dec. 1996.

Aberger et al. Mechanisms of Development, 54 (1) 23–37, Jan. 1996.

Database Medline, AN 89205518 . Hoyt et al. Am. J. Hematology 31 (1) : 50–52, May, 1989.

Database Medline, AN 97045853. White et al. Journal of Neurology, Neurosurgery and Psychiatry, 61 (4) : 369–375, Oct. 1996.

*Primary Examiner*—Michael P. Woodward
*Assistant Examiner*—Michael Borin
*Attorney, Agent, or Firm*—Griffin, Butler, Whisenhunt & Szipl, LLP

[57] ABSTRACT

The present invention refers to the use of Macrophage Stimulating Protein (MSP) for the preparation of a medicament for the treatment of pathologies of the central and peripheral nervous system of traumatic, infectious or inflammatory origin.

4 Claims, No Drawings

MACROPHAGE STIMULATING PROTEIN FOR THE TREATMENT OF PATHOLOGIES OF THE NERVOUS SYSTEM

The present invention refers to the use of Macrophage Stimulating Protein (MSP) for the preparation of a medicament for the treatment of pathologies of the central and peripheral nervous system of traumatic, infectious or inflammatory origin.

Macrophage Stimulating Protein (MSP) is a heterodimeric, kringle-containing growth factor belonging to the Hepatocyte Growth Factor family.

The biological functions of MSP are still largely unknown.

The MSP receptor is the tyrosine kinase encoded by the RON gene (Oncogene 11; 2627, 1995). It is expressed relatively late in murine development in specific areas of the central and peripheral nervous systems. Notably, high levels of the MSP receptor are found in two distinct areas: the nucleus of the trigeminal (V) nerve, known to contain elements migrated from the neural crest, and the nucleus of the hypoglossal (XII) nerve, thought to contain only motor neurons.

A number of growth factors, called neurotrophins, are potent and selective trophic factors for neurons in different districts of the nervous system. Among the activities of these molecules are the regulation of neuron growth and differentiation, and the sustaining of cell survival both in vivo and in vitro. Macrophage Stimulating Protein acts as a neuron survival factor, able to protect, as an example, motor neurons of the hypoglossal nucleus from degeneration following resection of the peripheral nerve.

The invention concerns therefore pharmaceutical compositions comprising as an active principle MSP for the treatment of any kind of impairment and degeneration of traumatic, infectious or inflammatory origin of the central and peripheral nervous system characterized by assonotmesis (axon degeneration) or neurotmesis (degeneration of axon and of the myeline sheath). Examples of said pathologies include:

phrenic nerve syndrome, resulting from surgical traumas or compression (for example aortic aneurysms);

brachial plexus disorders, usually caused by traumas, which can have different patterns depending on the concerned nerve roots;

lumbosacral disorders, due to traumas or compression;

some axon neuropathies due to toxic agents, for example saturnism in the case of lead poisoning.

For the considered therapeutic uses, the compositions of the invention may be administered by the intratechal, intraaracnideal, systemic (subcutaneous or intravenous) route or even by local administration, at the site of the thraumatic lesion.

The compositions of the invention will be formulated by means of known methods and excipients, such as disclosed in "Remington's Pharmaceutical Sciences Handbook", Mack Publishing Company, New York, U.S.A.

Particularly, sterile solutions or suspensions of MSP in suitable carriers, such as saline or glucose solutions and, generally, in any aqueous solution suited for the parenteral administration, will be used. The dosage of MSP will depend on several factors such as seriousness of the pathology, patient's weight, sex and age but, in general, a daily administration of a dosage ranging from 0.1 to about 100 mg of protein, for periods of a few weeks, is envisaged.

The invention also refers to the use of mutants of MSP as well as to precursors, fragments or engineered forms thereof.

The protein is preferably of human origin and is preferably obtained by means of recombinant DNA methods in suitable host cells.

Transduced cells able to express and secrete MSP or active forms thereof may also be directly implanted, for instance at the lesion site. The invention refers therefore also to expression vectors and to transduced cells for use in the therapy of the above mentioned pathologies.

Said vectors and cells may be prepared by conventional methods such as disclosed in Example 2 and by Gaudino et al. (EMBO J., 13:3524, 1994). Examples of cells suitable for the therapy of nervous lesions include glial cells (Mandel R J, Spratt S K, Snyder R O, Leff S E: *Midbrain injection of recombinant adeno-associated virus encoding rat glial cell line-derived neurotrophic factor protects nigral neurons in a progressive 6-hydroxydopamine-induced degeneration model of Parkinson's disease in rats.* Proc. Natl. Acad. Sci. USA 1997 Dec. 9; 94(25):14083–14088) and myoblasts (Deglon N, Heyd B, Tan S A, Joseph J M, Zurn A D, Aebischer P. *Central nervous system delivery of recombinant ciliary neurotrophic factor by polymer encapsulated differentiated C2C12 myoblasts.* Hum. Gene Ther. Nov. 10, 1996; 7(17):2135–2146).

The invention is illustrated in more detail in the following Examples.

EXAMPLE 1

MSP production and purification

The pro-MSP protein was produced with the Baculovirus expression system. The recombinant BacPAK-MSP Baculovirus, containing the full MSP cDNA (Genbank accession number L11924), was used to infect *Spodoptera frugiperda* insect cells (Sf9). Upon infection, proMSP was released in the culture supernatant, from which it was purified by subsequent steps of chromatography.

The conditions of infection were the following: Sf9 cells were grown in serum-free medium, maintained in exponential growth (max $5\times10^6$ cells/ml) in spinner bottles and passed every 48 h. Infection was carried out in serum free medium at the cell concentration of $10^6$ cells/ml. The optimal M.O.I. (Multiplicity Of Infection) was between 1.5 and 3. After 72 h, the supernatant was collected and clarified by centrifugation.

Pro-MSP was purified from Sf9-conditioned medium by affinity chromatography on heparin column followed by ion exchange chromatography and ultrafiltration. Clarified medium was dialyzed against 10 mM phosphate buffer, pH 6.7, 0.2 M NaCl, and loaded onto a heparin column washed with the dialysis buffer supplied with 0.01% Tween 80. Pro-MSP was eluted with linear NaCl gradient from 0.2 M to 0.8 M in 10 mM phosphate buffer, pH 6.7 (MSP activity was recovered between 0.45 M and 0.6 M). MSP-containing fractions were diluted to a final NaCl concentration of 0.1 M in 10 mM phosphate buffer, pH 6.7, and loaded onto a ion exchange CM Sepharose column (Pharmacia), washed with 0.1 M NaCl, 10 mM phosphate buffer, pH 6.7. Pro-MSP was eluted with a linear NaCl gradient from 0.1 to 25 M. The peak of MSP activity was recovered between 0.15 M and 0.18 M. Finally, the pro-MSP-containing fractions were concentrated by ultrafiltration using columns with a cutoff of 30 kDa.

Pro-MSP activation to the bioactive MSP molecule was performed by incubation at 37° C. for 18 hours in the presence of 10% FCS.

EXAMPLE 2

Neuro2A cell transfection

Neuro2A cells were grown in DMEM supplemented with 10% FCS to 60% confluence and transfected with the pBat-MSP vector or a control vector (10 µg/plate) with the calcium phosphate method. Cells were glycerol shocked 12 hours after transfection and collected after 72 hours by ATV. They were pelleted and incubated in DiI for 1 hour at 37° C. before injection.

EXAMPLE 3

Effect of MSP-producing cells on the proximal stump 12 adult albino mice of our breeding colony were used for this study. All of them were anaesthetized with a 1:1 mixture of ketamine hydrochloride and xyalzine and had their left hypoglossal nerve cut at its emergence close to the lateral side of the digastricus muscle. According to the experimental protocol (i) four of them were hold in a Stoelting stereotaxic apparatus and injected at the pontobulbar junction with a glass micropipette (tip diameter 30 µm) with a suspension of control Neuro2A cells (one mouse) or with MSP-transfected N2A cells (three mice); (ii) three of them had N2A cells (either control, one mouse, or MSP-transfected, two mice) placed close to the proximal stump of the cut hypoglossal nerve; (iii) three mice had an Alzet minipump filled with MSP (two mice) or with a control solution (one mouse) placed in the pectoral region, with the catheter positioned close to the proximal stump of the nerve; (iv) two mice received no further treatment. All mice were allowed to recover from surgery and sacrificed with an overdose of anaesthetics one week after surgery. They were perfused through the left ventricle with a saline washing solution followed by the fixative (4% paraformaldehyde in 0.1 M phosphate buffer, pH 7.4).

The brainstem was dissected out of the skull, fixed for 4 hours and immersed in PBS containing 30% sucrose O/N for cryoprotection. 50 µm-thick transverse sections were cut at the cryostat and reacted free-floating with an antibody against Choline Acetyl Transferase (Chemicon), revealed by the avidin-biotin system using diamino benzidine as chromogen. Slices were then mounted on gelatin-coated slides, dehydrated and mounted in Entellan. Slides were observed and photographed with a Leitz Dialx light microscope. The cell size of ChAT-positive cells in the hypoglossal nucleus of both sides was measured by using a motorized stage interface to an IBM personal computer and the Neurolucida software (Microbrightfiled Inc., Vt).

Results

Motor neurons of the hypoglossal nucleus undergo degeneration and death within a week after lesion of the peripheral nerve, as shown by localized disappearance of CHAT immunoreactivity in brainstem sections. We tested the activity of MSP-producing cells or by local administration of the purified active molecule.

Effect of MSP-producing cell implant at the proximal stump

Neuro2A cells transfected with the complete MSP cDNA (N2A/MSP) or with a control plasmid (N2A/pBAT) were implanted at the proximal stump of cut hypoglossal nerves (about 300.000 cells/implant). The presence of MSP-producing cells largely prevented the lesion-induced neuron death, as shown by sustained ChAT immunoreactivity on hypoglossal nucleus sections. The implant of N2A/pBAT control cells had no protective effect against neuron degeneration.

|  | N2A/pBAT | N2A/MSP |
|---|---|---|
| Motoneuron count (cells/field) | 10 ± 3 | 27 ± 4 |

Effect of MSP delivery at the proximal stump through Alzet minipumps.

The retrograde degeneration of hypoglossal motor neurons could also be prevented by continuous infusion of purified MSP (400 ng/ml) for a week at the proximal stump of the cut nerve. The administration of the factor protected neurons from degeneration to an extent comparable to the implant of MSP-producing cells.

|  | Control | MSP |
|---|---|---|
| Motoneurons count (cells/field) | 12 ± 5 | 32 ± 6 |

We claim:

1. A method of treatment of peripheral nerve degeneration of traumatic origin comprising administering to an animal in need of said treatment a medicament containing a treatment effective amount of Macrophage Stimulating Protein (MSP).

2. The method of claim 1, wherein the trauma is trauma to a nerve myelinic sheath.

3. The method of claim 1, which comprises infusing purified MSP at a site of a nerve trauma.

4. The method of claim 3, which comprises providing a continuous infusion of approximately 400 ng/ml of MSP at said site.

* * * * *